United States Patent [19]
Desai et al.

[11] Patent Number: 5,834,556
[45] Date of Patent: Nov. 10, 1998

[54] GRAFT COPOLYMER OF POLYCATIONIC SPECIES AND WATER-SOLUBLE POLYMERS, AND USES THEREFOR

[75] Inventors: Neil P. Desai; Patrick Soon-Shiong; Paul A. Sandford; Roswitha E. Heintz, all of Los Angeles, Calif.

[73] Assignee: Vivorx, Inc., Santa Monica, Calif.

[21] Appl. No.: 697,885

[22] Filed: Aug. 29, 1996

Related U.S. Application Data

[62] Division of Ser. No. 856,137, Mar. 23, 1992, Pat. No. 5,578,442.

[51] Int. Cl.$^6$ ............................. C08G 63/48; C08G 63/91
[52] U.S. Cl. .................... 525/54.1; 525/54.2; 525/54.21; 525/54.23; 525/54.24; 525/54.26; 525/54.3; 525/54.31; 525/60; 525/63; 525/64; 525/70; 527/200; 527/201; 527/207; 527/300; 527/311; 527/312; 527/313; 527/314
[58] Field of Search .................................. 525/54.1, 54.2, 525/54.21, 54.23, 54.24, 54.26, 54.3, 54.31, 60, 63, 64, 70; 527/200, 201, 207, 300, 311, 312, 313, 314

[56] References Cited

U.S. PATENT DOCUMENTS

| | | | |
|---|---|---|---|
| 5,334,640 | 8/1994 | Desai et al. | 524/56 |
| 5,380,536 | 1/1995 | Hubbell et al. | |
| 5,573,934 | 11/1996 | Hubbell et al. | 435/177 |

FOREIGN PATENT DOCUMENTS

WO 91/07951   6/1991   WIPO.

OTHER PUBLICATIONS

Ruegg and Hefti, "Growth of Dissociated Neurons in Culture Dishes Coated with Synthetic Polymeric Amines", Neuroscience Letters, vol. 49:319–324 (1984).

Epstein and Lunney, "A Cell Surface ELISA in the Mouse Using Only Poly–L–Lysine as Cell Fixative", Journal of Immunological Methods vol. 76:63–72 (1985).

Harris, Milton J., "Laboratory Synthesis of Polyethylene Glycol Derivatives", Macromol. Chem. Phys. vol. C25(3):325–373 (1985).

Nagaoka and Nakao, "Clinical application of antithrombogenic hydrogel with long poly(ethylene oxide) chains", Biomaterials vol. 11:119–121 (1990).

Zheng et al., Prolonged Pancreas Preservation Using a Simplifed UW Solution Containing Polyethylene Glycol, vol. 51:63–66 (1991).

Desai and Hubbell, "Biological responses to polyethylene oxide modified polyethylene terephthalate surfaces", Journal of Biomedical Materials Research vol. 25:829–843 (1991).

Desai and Hubbell, "Solution technique to incorporate polyethylene oxide and other water soluble polymers into surfaces of polymeric biomaterials", Biomaterials vol. 12:144–152 (1991).

*Primary Examiner*—Nathan M. Nutter
*Attorney, Agent, or Firm*—Stephen E. Reiter; Gray Cary Ware & Freidenrich; Gregory P. Raymer

[57] ABSTRACT

In accordance with the present invention, there are provided methods to render cells non-adhesive and/or non-immunogenic with respect to macromolecules typically encountered in culture media or in physiological media.

15 Claims, No Drawings

GRAFT COPOLYMER OF POLYCATIONIC SPECIES AND WATER-SOLUBLE POLYMERS, AND USES THEREFOR

This application is a divisional of application Ser. No. 07/856,137, filed on Mar. 23, 1992 and now U.S. Pat. No. 5,578,442.

The present invention relates to methods for rendering cells non-adhesive. In another aspect, the present invention relates to methods for rendering cells non-immunogenic. In yet another aspect, the present invention relates to methods for the stabilization of liposomes. In a further aspect, the present invention relates to methods for the in vitro generation of neural networks.

BACKGROUND OF THE INVENTION

Water-soluble polymers, such as polyethylene glycols (PEGs), have been investigated extensively in recent years for use as biocompatible, protein repulsive, noninflammatory, and nonimmunogenic modifiers for drugs, proteins, enzymes, and surfaces of implanted materials. These characteristics have variously been attributed to a combination of properties of such polymers, e.g., nonionic character, water solubility, backbone flexibility, and volume exclusion effect in solution or when immobilized on a surface.

While extensive efforts have been made to render foreign substances, such as drugs, proteins, and the like, non-immunogenic employing water-soluble polymers such as PEG, the use of such polymers to render an individual cell non-immunogenic has not been considered in the art. If such polymers could be attached directly to a cell surface, then it is possible, due to the exclusion of proteins and macromolecules from the vicinity of the cell surface, that the cell as a whole may be rendered non-immunogenic. The ability to accomplish such attachment would be invaluable for a variety of treatment protocols.

It is known that mammalian cell membranes have a variety of negatively charged species on their exterior. For example, negatively charged proteoglycans (PGA), glycosaminoglycans (GAG), such as chondroitin sulfate and heparin sulfate, and negatively charged lipids have all been identified on cell exteriors. Not surprisingly, polycation species such as polylysine and polyornithine interact with negatively charged cell surfaces to form a strong ionic linkage. Unfortunately, polycations (such as polylysine and polyornithine) are known to be cytotoxic, even at fairly low concentrations. Polylysine, for example, has been used as a cell fixative, and has been shown to cause cell aggregation (e.g., with human platelets).

While water-soluble polymers, having found use in a variety of biological applications, would be ideal for use in treating cells to render them non-immunogenic, their generally non-ionic nature renders them substantially unable to bind to cell membranes. Thus, for example, treatment of cells with unmodified PEG was unable to confer a non-adhesive or protein repellant character on such cells.

BRIEF DESCRIPTION OF THE INVENTION

In accordance with the present invention, we have developed methods to render cells non-adhesive and/or non-immunogenic with respect to macromolecules typically encountered in culture media or in physiological media.

The methods of the present invention can be used for a wide variety of purposes, e.g., for the treatment of cells used for implantation (thereby avoiding the need for immunosuppressive therapy), for the preservation of organs outside the body while awaiting transplant, for modifying surfaces of materials which are to be exposed to various components of physiological media, for the stabilization of liposomes (and prevention of their uptake by the reticuloendothelial system), and the like.

DETAILED DESCRIPTION OF THE INVENTION

In accordance with the present invention, there is provided a method to render cells non-adhesive, said method comprising contacting said cells with an effective amount of a composition comprising a polycationic species having water-soluble polymer chains grafted thereon.

As employed herein, reference to rendering cells "non-adhesive" means, in an in vitro setting, that cells do not stick to wells (e.g., glass, plastic, and the like), or other surfaces with which they come in contact. Instead, non-adhesive cells, as contemplated herein, spread and grow, yet remain in suspension. In an in vivo setting, "non-adhesive" refers to cells which do not adhere to biologically-encountered macromolecules or proteinaceous matrix (e.g., collagen matrix). As used herein, "non-adhesive" also refers to cells which have been rendered non-immunogenic, i.e., cells which are substantially non-susceptible to an immune response mediated by biological macromolecules.

"Contacting" of cells or tissues with graft copolymer compositions contemplated for use in the practice of the present invention is typically carried out in vitro at room temperature for a time in the range of about 0.01 up to 1 hour or longer in suitable physiological buffer (i.e., pH in the range of about 7.2–7.4; osmolarity of about 290 mOsm/kg) containing a concentration of at least about 0.005% of graft copolymer, with respect to the concentration of the polycationic species used for the preparation of the cell surface (e.g., polylysine). It is presently preferred to treat cells with a solution of graft copolymer containing a concentration of graft copolymer in the range of about 0.05 up to 1.0%, with concentrations of graft copolymer in the range of about 0.1 up to 0.5% being especially preferred. Those of skill in the art recognize that as the molecular weight of the polycationic species is increased, a lower concentration (determined on the same basis as set forth above) of the graft copolymer is required to produce the same beneficial effect.

As employed herein, an "effective amount" of graft copolymer compositions contemplated for use in the practice of the present invention is an amount sufficient to render said cells non-adhesive to biological macromolecules, while leaving the cells viable (as determined, for example, by suitable staining techniques). In the case of specialized cells, such as islets, it is desirable for the treated cells to retain their unique function as well as viability (i.e., the ability of islets to respond to exposure to glucose by secretion of insulin). Typically, an excess of graft copolymer is used with respect to the negative charges present on the surface of the cells to be treated. The quantity of graft copolymer required will vary depending on the cell type being treated and the concentration of cells to be treated. Typically, in the range of about $10^{2-10^8}$ cells/ml will be treated. For example, up to about $10^8$ bacterial cells/ml, up to about 100,000 fibroblasts/ml, or up to about 50,000 islets/ml will be treated.

Copolymer compositions contemplated for use in the practice of the present invention comprise a polycationic species having water-soluble polymer chains grafted thereon. Polycationic species contemplated for use in the practice of the present invention are polycationic species having sufficient charge density to allow binding of the above-described graft copolymer to cells, and include:
polymers containing primary amine groups, secondary amine groups, tertiary amine groups or pyridinyl nitrogen (s), such as polyethyleneimine, polyallylamine, polyetheramine, polyvinylpyridine, and the like, polysaccharides having a positively charged functionality thereon (e.g., chitosan), polyamino acids, such as:

poly-L-histidine, poly-im-benzyl-L-histidine, poly-D-lysine, poly-DL-lysine, poly-L-lysine, poly-ε-CBZ-D-lysine, poly-ε-CBZ-DL-lysine, poly-ε-CBZ-L-lysine, poly-DL-ornithine, poly-L-ornithine, poly-δ-CBZ-DL-ornithine, poly-L-arginine, poly-DL-alanine-poly-L-lysine;

poly(-L-histidine, L-glutamic acid)-poly-DL-alanine-poly-L-lysine;

poly(L-phenylalanine, L-glutamic acid)-poly-DL-alanine-poly-L-lysine;

poly(L-tyrosine, L-glutamic acid)-poly-DL-alanine-poly-L-lysine;

random copolymers of:

L-arginine with tryptophan, tyrosine, or serine;

D-glutamic acid with D-lysine;

L-glutamic acid with lysine, ornithine, or mixtures thereof;

and the like, as well as mixtures of any two or more thereof.

Presently preferred polycations for use in the practice of the present invention include polylysine (i.e., poly-D-lysine (PDL), poly-DL-lysine, poly-L-lysine (PLL), poly-ε-CBZ-D-lysine, poly-ε-CBZ-DL-lysine, or poly-ε-CBZ-L-lysine), polyornithine (i.e., poly-DL-ornithine, poly-L-ornithine or poly-δ-CBZ-DL-ornithine), and the like.

Polycationic species having a wide range of molecular weights can be employed in the practice of the present invention. Polycations having a MW in the range of about 200 up to 1,000,000 are suitable, with molecular weights in the range of about 1000 up to 100,000 preferred. Presently most preferred polycationic species for use in the practice of the present invention will have molecular weights in the range of about 5,000 to 50,000.

Optionally, the polycationic species employed in the practice of the present invention can be further modified with one or more functional groups capable of undergoing free radical polymerization. Suitable functional groups for this purpose include unsaturated species capable of free radical polymerization, such as, for example, acrylate groups, vinyl groups, methacrylate groups, and the like. When cells or tissues are treated with such modified polycationic species, the graft copolymer can be further subjected to free radical polymerization conditions, thereby stabilizing the association of graft copolymer with the cell surface. In addition, the further crosslinking of the graft copolymer forms a highly stabilized, immunoprotective coating of water-soluble polymer about the treated cell or tissue.

Free radical polymerization of the above-described modified polycationic species can be carried out in a variety of ways, for example, initiated by irradiation with suitable wavelength electromagnetic radiation (e.g., visible or ultraviolet radiation) in the presence of a suitable photoinitiator, and optionally, cocatalyst and/or comonomer. Alternatively, free radical polymerization can be initiated by thermal decomposition of a suitable free radical catalyst, such as benzoyl peroxide, azobisisobutyronitrile, and the like.

Photoinitiators contemplated for use in the practice of the present invention include such ultraviolet (UV) initiators as 2,2-dimethyl phenoxyacetophenone, benzophenones and ionic derivatives (for water solubility), benzils and ionic derivatives thereof, thioxanthones and ionic derivatives thereof; and visible photoinitiators such as ethyl eosin, eosin, erythrosin, rose bengal, thionine, methylene blue, riboflavin, and the like.

Cocatalysts are typically used when the excited state of the photoinitiator is quenched too rapidly to efficiently promote polymerization. In such a situation, a cocatalyst (also referred to in the art as a "cosynergist", "activator", "initiating intermediate" or "quenching partner") will generally be employed. Cocatalysts contemplated for use in the practice of the present invention include triethanolamine, methyl diethanolamine, triethylamine, arginine, and the like.

Water-soluble polymeric species contemplated for use in the practice of the present invention are water-soluble polymers capable of rendering polycations non-immunogenic and include non-ionic, water-soluble polymers such as polyethylene glycol (PEG), polyvinyl alcohol (PVA), poly(hydroxyethyl methacrylate) (pHEMA), poly(acrylamide), poly(vinyl pyrrolidone) (PVP), poly(ethyl oxazoline), polysaccharides (such as, for example, starch, glycogen, guar gum, locust bean gum, dextran, levan, inulin, cyclodextran, agarose, and the like); as well as ionic, water-soluble polymers such as polyacrylic acid (PAA) or polysaccharides (such as, for example, xanthan gum, carageenan, hyaluronic acid, heparin, chitosan, pectin, and the like); as well as copolymers of any two or more of said water-soluble polymeric species. Presently preferred water soluble polymers employed in the practice of the present invention are polyalkylene oxides, such as polyethylene glycol (PEG).

Water-soluble polymeric species having a wide range of molecular weights can be employed in the practice of the present invention. Polymeric species having a MW in the range of about 200 up to 1,000,000 are suitable, with molecular weights in the range of about 500 up to 100,000 preferred. Presently most preferred polymeric species for use in the practice of the present invention will have molecular weights in the range of about 1000 to 50,000.

Optionally, the water-soluble polymeric species employed in the practice of the present invention can be further modified with one or more functional groups capable of undergoing free radical polymerization. Suitable functional groups for this purpose include unsaturated species capable of free radical polymerization, such as, for example, acrylate groups, vinyl groups, methacrylate groups, and the like. When cells or tissues are treated with such modified water-soluble polymeric species, the graft copolymer can be further subjected to free radical polymerization conditions, thereby stabilizing the association of graft copolymer with the cell surface. In addition, the further crosslinking of the graft copolymer forms a highly stabilized, immunoprotective coating of water-soluble polymer about the treated cell or tissue.

Free radical polymerization of the above-described modified water-soluble polymeric species can be carried out in the same manner as described above with respect to free radical polymerization of modified polycationic species.

Graft copolymers contemplated for use in the practice of the present invention are those wherein the polycationic species has grafted thereon at least one water-soluble polymer chain per chain of said polycationic species, up to a maximum of one grafted chain per repeat unit of said polycationic species. For example, when the molecular weight of the polycationic species falls in the range of about 20,000, it will typically have grafted thereon at least about 5 chains of said water-soluble polymer chain per chain of polycationic species; with in the range of about 10–20 chains of said water-soluble polymer chain per chain of said polycationic species being the presently most preferred level of grafting. Those of skill in the art recognize that with polycationic species having higher molecular weights, higher levels of grafting will be desirable, and that the above values for grafting levels should be increased accordingly. Similarly, with respect to the water-soluble component of invention graft copolymers, the use of higher molecular weight species will allow one to achieve substantially the same result while grafting fewer (water-soluble) chains per chain of polycationic species.

Preparation of the graft copolymers of the present invention can be carried out employing chemical techniques known by those of skill in the art. For example, the free hydroxyl groups of the water-soluble component can be activated to render such groups susceptible to nucleophilic displacement. Thus, the free hydroxyl groups of the water-soluble component can be subjected to esterification, etherification, amidation, urethane formation, and the like. Such reactions involve the generation of such intermediates as carbonates, sulfonates, xanthates, epoxides, aliphatic aldehydes, carboxymethyl azides, succinimidyl succinates, and the like. The activated water-soluble component can then be coupled to a suitable polycationic species, for example, by nucleophilic displacement.

Cell types contemplated for use in the practice of the present invention include islets, fibroblasts, thyroid cells, parathyroid cells, adrenal cells, neuronal cells, dopamine secreting cells, hepatocytes, nerve growth factor secreting cells, adrenaline/angiotensin secreting cells, norepinephrine/metencephalin secreting cells, human T-lymphoblastoid cells sensitive to the cytopathic effects of HIV, and the like.

Also included within the scope of the present invention are cells having a modified cell surface which is substantially non-adhesive with respect to macromolecules encountered in physiological environments.

In accordance with another embodiment of the present invention, there is provided a process to remove copolymer compositions contemplated for use in the practice of the present invention from cells treated as described above, said process comprising contacting such cells with an effective amount of an anionic species.

Anionic species contemplated for use in this embodiment of the present invention include monomeric or polymeric anions. Any soluble anionic species capable of reversing the association of polycationic species with negatively charged cell surface can be employed for this purpose. Presently preferred anionic species are polyanionic species, such as, for example, heparin, heparin sulfate, chondroitin sulfate, soluble alginates (e.g., sodium alginate, potassium alginate, ammonium alginate, and the like), bovine serum albumin, hyaluronic acid, pectin, carageenan, oxidized cellulose, and the like.

"Contacting" of treated cells to remove invention copolymer therefrom is carried out at room temperature for a time in the range of about 0.01 up to 1 hour or longer in physiological buffer solution containing anionic species at a sufficiently high ionic strength to reverse the association of polycationic species with negatively charged cell surface.

An effective amount of anionic species to employ in accordance with this embodiment of the present invention depends on the specific anionic species employed. Generally, the concentration of anionic species employed will be sufficient to reverse polycation binding to cells or tissues, but not so high as to be toxic to the biological material being treated. Concentrations employed are typically in excess of the amount of anion actually needed to disrupt binding of polycation to cell surface. Thus, for example, presently preferred treating solutions contain about 2.5 Units/ml of heparin or 2 mg/ml of bovine serum albumin.

In accordance with yet another embodiment of the present invention, there is provided a method to render cells non-immunogenic, said method comprising contacting said cells with an effective amount of a composition comprising a polycationic species having water-soluble polymer chains grafted thereon.

"Contacting" of cells with graft copolymer compositions to render cells non-immunogenic is typically carried out as described above with respect to rendering cells non-adhesive.

The process of the present invention can be used for rendering non-immunogenic any cell, tissue, organ, or system of organs, and the like, that may be used for transplant or the like.

Also included within the scope of the present invention are cells having a modified cell surface which is substantially non-immunogenic with respect to mediators of immune response, e.g., biological macromolecules such as proteins, enzymes, and the like.

In accordance with another embodiment of the present invention, there is provided a process to remove copolymer compositions contemplated for use in the practice of the present invention from cells treated as described above, said process comprising contacting treated cells with an effective amount of an anionic species, as described above.

In accordance with still another embodiment of the present invention, there is provided a method to preserve cells and/or tissues which are subjected to long periods of storage before being used for therapeutic applications, said method comprising contacting said cells and/or tissues with an effective amount of a composition comprising a polycationic species having water-soluble polymer chains grafted thereon. "Contacting" of cells and/or tissues with graft copolymer compositions to preserve same is typically carried out as described above with respect to rendering cells non-adhesive and/or non-immunogenic.

In accordance with a still further embodiment of the present invention, there is provided a method for associating water-soluble polymer with a cell surface, said method comprising:

grafting water-soluble polymer onto a polycationic resin to produce a copolymer of said water-soluble polymer and said polycation, and thereafter contacting said cell surface with an effective amount of said copolymer.

If desired, the copolymer can be substantially removed from the cell surface employing the above-described removal process.

In accordance with a further embodiment of the present invention, there is provided a method for the stabilization of liposomes having negatively charged surfaces, said method comprising contacting said liposomes with an effective, stabilizing amount of a composition comprising a polycationic species having water-soluble polymer chains grafted thereon.

"Contacting" of liposomes for the stabilization thereof is carried out at room temperature for a time in the range of about 0.01 up to 1 hour or longer in physiological buffer.

An effective amount of graft copolymer for use in this embodiment of the present invention is an amount sufficient to render such liposomes essentially non-detectable in vivo, thereby reducing uptake of the liposome by the reticuloendothelial system (and increasing liposome circulation times in vivo). Suitable quantities of graft copolymer will render the liposomes substantially non-adhesive to biological materials, while leaving the liposome intact, and without adversely affecting the function and/or activity of the contents thereof, if any. Typically, a concentration of graft copolymer sufficient to neutralize the negative charges on the surface of the liposome will be employed. Concentrations in the range of at least about 0.05% of graft copolymer, with respect to the concentration of the polycationic species used to treat the surface of said liposome will be employed; with concentrations of graft copolymer in the range of about 0.1 up to 0.5% being presently preferred.

One can readily determine the stability of a liposome using a functional assay, such as the following. In an in vitro setting, the stability of liposome-encapsulated hemoglobin in an un-modified liposome could be compared to the stability of hemoglobin encapsulated in a liposome stabilized in accordance with the present invention (i.e., the result of treating an un-modified liposome with a sufficient quantity of graft copolymer described above to stabilize the liposome). The release of hemoglobin into the surrounding buffer media over time would then be assayed, with an extended time-frame for release of hemoglobin indicating enhanced liposome stability.

In accordance with yet another embodiment of the present invention, there is provided a method for producing neural networks on a substrate, said method comprising:

masking that portion of said substrate which defines the desired network, rendering the unmasked portion of said substrate non-adhesive by the above-described method of the invention, removing the mask, then allowing cells to spread and grow on said substrate, wherein cells grow only on the portion of the substrate which has not been treated with graft copolymer.

Substrates contemplated for use in the above-described method include tissue culture substrates, such as collagen, tissue culture polystyrene, microporous dextran substrate, and the like.

Masking contemplated by the above-described method can be accomplished in a variety of ways, such as, for example, by covering a portion of the substrate with an agent which does not serve as a substrate for cell growth (e.g., a piece of tape, or the like).

The masking agent employed can readily be removed by merely reversing the process employed for applying the mask to the substrate.

Conditions required for cells to spread and grow on the substrate are standard cell culture conditions.

The resulting neural networks can be used for a variety of purposes, such as, for example, for studying the transmission of nerve impulses, for connection between a nerve cell and an electrical circuit, and the like.

The invention will now be described in greater detail by reference to the following non-limiting examples.

EXAMPLES

Example I

Synthesis of a Graft copolymer of Poly-L-Lysine and Polyethylene Glycol

Twenty grams (20 g) of PEG (molecular weight 10,000 g/mol, having the structure HO-PEG-OH) were dried in a vacuum oven at 80° C. for 24 hours and dissolved in 100 ml of methylene chloride that had been dried by molecular sieves (4A). Then, 3.24 g of 1,1-carbonyldiimidazole (CDI, 5 fold excess, to ensure the activation of 100% of PEG end groups) were added to the solution and stirred overnight at room temperature in an argon atmosphere. The CDI-activated PEG was then precipitated with an excess of anhydrous diethyl ether and dried overnight under vacuum. Five grams (5 g) of the CDI-activated PEG were dissolved in 20 ml of 5 mM sodium borate buffer (pH 9). In order to prevent crosslinking of poly-L-lysine (PLL) with the 100% CDI-activated PEG, 50% of the PEG end groups were inactivated by adding 30.2 gl of ethanolamine to the buffer solution and stirring for 4–6 hours at room temperature. This results in a mono-activated CDI-derivative of PEG, having the structure CDI-PEG-OH. Alternatively, a monomethoxy PEG could be used to avoid this partial deactivation step, but monomethyl PEGs are presently available commercially only up to molecular weight 5000.

Following the above-described partial deactivation step, 50 mg of PLL (M.W. 20,100 g/mol) were added to the reaction mixture and stirred for 24 hours at room temperature. The solution was then dialyzed for 24 hours against deionized water and freeze dried to obtain a powder. This procedure produced a PEG graft copolymer (PLL-PEG) having a concentration of approximately 10–20 PEG chains per PLL chain.

Example II

Demonstration of Cell Binding Properties of PLL-PEG to Fibroblasts: Effect on Cells in Suspension The cell binding effects of PLL-PEG copolymer produced as described in Example I were tested on cultures of human foreskin fibroblasts (HFF). These cells are anchorage dependent and ordinarily die within 4 to 10 hours if they do not adhere and spread on a surface. Thus, a flask of confluent HFF was harvested with trypsin-EDTA, then the resultant cells in suspension were split into 6 batches, each containing approximately 170,000 cells. Each batch was centrifuged to obtain cell pellets. Six different solutions were used for cell treatment:

(A) Fibroblast culture media: Dulbecco's modified Eagles' medium (D-MEM) containing 10% fetal bovine serum;

(B) 10 mM HEPES buffered saline (HBS), pH 7.4;

(C) HBS containing 0.1% (w/v) PLL;

(D) HBS containing 0.5% PEG (M.W. 10,000);

(E) HBS containing 0.1% PLL and 0.5% PEG; and (F) HBS containing 0.3% PLL-PEG (based on PLL concentration).

All solutions were sterilized by filtration through 0.22 micron filters prior to use. The cell pellets were resuspended in 2 ml of solutions A, B, C, D, E or F for approximately 10 minutes. The tubes were then centrifuged (200 xg for 5 minutes), the solutions aspirated and replaced with fibroblast culture medium, and the cells plated onto culture dishes. The plated cells were observed periodically to verify adherence and spreading. The cells were also stained with trypan blue (TB) to test viability. Table I summarizes the observations over 5 days following the seeding.

TABLE I

HFF TREATMENT SOLUTIONS

| TIME AFTER SEEDING | A (fibroblast culture medium) | B (buffered saline) | C (PLL) | D (PEG) | E (PLL + PEG) | F (PLL-PEG copolymer) |
|---|---|---|---|---|---|---|
| 1 hr | Normal spreading | Normal spreading | No adherence; Cell clumping | Normal spreading | No adherence; Cell clumping | No adherence; No clumping |

TABLE I-continued

HFF TREATMENT SOLUTIONS

| TIME AFTER SEEDING | A (fibroblast culture medium) | B (buffered saline) | C (PLL) | D (PEG) | E (PLL + PEG) | F (PLL-PEG copolymer) |
|---|---|---|---|---|---|---|
| % viability 24 hr | 95 Normal spreading | 95 Normal spreading | 0 No adherence; Cell clumping | 90 Normal spreading | 0 No adherence; Cell clumping | 80 No adherence; No clumping |
| % viability 48 hr | 100 Confluent monolayer | 100 Confluent monolayer | 0 No adherence; Cell clumping | 95 Confluent monolayer | 0 No adherence; Cell clumping | 70 No adherence; No clumping |
| % viability 120 hr | 100 Confluent monolayer | 100 Confluent monolayer | 0 No adherence; Cell clumping; Few spread Cells | 95 Confluent monolayer | 0 No adherence; Cell clumping; Few spread Cells | 60 No adherence; No clumping; Few spread Cells |
| % viability | 100 | 100 | <1 | 95 | <3 | 60 |

Treatments A, B, and D showed essentially the same results, with most of the HFF showing normal spreading and viability.

Free PLL was found to be toxic at the concentrations used (treatments C and E). Essentially all cells subjected to treatments C and E took up TB and did not spread on the tissue culture substrate. The cells subjected to treatments C and E also showed extensive aggregation.

Free PEG had no appreciable effect on cell function (treatment D). PEG also had no appreciable ameliorating effect in conjunction with PLL (treatment E).

Incubation with the graft PLL-PEG copolymer of the present invention (treatment F) however, had a remarkable effect on the HFF. In stark contrast to treatment with free PLL, treatment with the copolymer PLL-PEG (at 3 times higher concentration than used for treatments C and E) produced cells that showed no adherence to the substrate, no aggregation in suspension, but a high percent viability. This viability was maintained for well over 24 hours with the HFF still in suspension. This behavior is quite unusual for anchorage dependent cells.

A distinct morphological difference in cells treated with PLL and PLL-PEG was evident. PLL treated cells in suspension showed a rough or ragged surface while those treated with PLL-PEG copolymer of the present invention are smooth and spherical, much like freshly trypsinized cells.

These results indicate that treatment with the PLL-PEG copolymer of the invention is noncytotoxic to HFF. In addition, interaction of the PEG-grafted polycation with the exterior of the cell prevents the cell from adhering to a substrate. Thus the cytotoxicity of PLL is markedly reduced by PEG grafting.

Five days after the initial treatment, a few of the cells treated with PLL-PEG copolymer begin to show some spreading on the surface of the culture dish. This observation implies that the PLL-PEG copolymer may either have desorbed from the cell surfaces, or cell division may have occurred (which would dilute the concentration of PLL-PEG copolymer on the cell membrane).

Example III

Assessment of Efficacy of PLL and PLL-PEG Treatments at Various Dilutions

A similar experiment as outlined in Example II was conducted to test the effects of PLL and PLL-PEG copolymer at various dilutions. Solutions C and F were serially diluted with 10 mM HEPES buffered saline (HBS) to $1/5$, $1/25$, and $1/125$ of their original concentrations, and human foreskin fibroblasts (HFF) incubated in these solutions for 10 minutes. Additional treatments included PEG 20M (a PEG composition having a molecular weight of about 20,000, comprised of two lower molecular weight PEGs (one having a MW ~8,000 and the other having a MW of ~10,000) linked together by a hydrophobic, bifunctional bisphenol-epichlorohydrin linker; available from Union Carbide, Danbury, Conn.) and PEG 20,000 (a substantially linear PEG having a molecular weight of ~20,000; available from Fluka, Ronkonkoma, N.Y.) at 0.5% in HBS. A control treatment with fibroblast culture media was also run. Results are summarized in Table II, below.

In the Table, the following abbreviations are used:

"adh." for adhesion,

"aggreg." for aggregated, and

"subst." is the abbreviation for substrate.

P-0 refers to cells treated with 0.1% of PLL, and P-5, P-25 and P-125 refer to cells treated with 1/5, 1/25, and 1/125 dilutions thereof, respectively. Similarly, G-0 refers to cells treated with 0.3% of PLL-PEG copolymer, and G-5, G-25 and G-125 refer to cells treated with $1/5$, $1/25$, and $1/125$ dilutions thereof, respectively.

TABLE II

HFF TREATMENT SOLUTIONS

| TIME AFTER SEEDING | Control | | | PLL treatment | | | | PLL-PEG copolymer treatment | | | |
|---|---|---|---|---|---|---|---|---|---|---|---|
| | No PEG | 20 M PEG | 20,000 PEG | P-0 | P-5 | P-25 | P-125 | G-0 | G-5 | G-25 | G-125 |
| 0 hr | | Minor adh. to substr. | | Clumped | Clumped | Clumped | Clumped; adh. to subst. | No adh. | No adh. | Minor adh. to subst. | Minor adh. to subst. |
| 3 hr | | 100% adh. to subst. | | Clumped; aggreg.; no adh. to subst. | Clumped; aggreg.; no adh. to subst. | Clumped; 5–10% adhered to subst. | Clumped; 5–10% adhered to subst. | No adh. | 50% adh. | 75% adh. to subst. | 100% adh. to subst. |
| 24 hr | | 100% adhesion | | No adh; Extensive clumping | No adh; Extensive clumping | Clumped; ~10% adh. to subst. | Clumped; ~10% adh. to subst. | No adh.; no clumping | ~60% adh.; | ~80% adh. | ~100% adhesion |
| % viability | | 100% | | <10% | <10% | <10% | <10% | >70% | >70% | >70% | >70% |

Observation of the cells immediately after seeding showed all PLL treatments (abbreviated P) to cause clumping of cells. A small number of cells showed adherence in the P-125 treatment. The graft copolymer (PLL-PEG, abbreviated G) treatment showed a decrease in efficacy at the lower concentrations. At dilutions of 25 and 125 (G-25 and G-125), adherence of cells was noted, though not quantified. Treatments with the PEG 20M and PEG 20,000 showed no appreciable difference from the control.

Three hours following the initial seeding, the following observations were made. The PLL treated cells P-0 (0.1% PLL) and P-5 were clumped and aggregated, with none of the cells showing adherence to the substrate. P-25 and P-125 also showed clumping, but approximately 5–10% of cells adhered to the substrate, indicating PLL cytotoxicity at very low concentrations.

Cells treated with PLL-PEG showed an increased adhering tendency with increasing dilutions. G-0 (0.3% PLL-PEG) showed no adhesion and individual free-floating cells. G-5, G-25, and G-125 showed approximately 50%, 75% and 100% adherence, respectively, at 3 hours. G-125 was very similar to the PEGs and the control.

After 24 hours, P-0 and P-5 showed no adherence to substrate, and extensive clumping. P-25 and P-125 also showed clumping, but approximately 10% of the cells were adhered to the substrate, indicating a lower level of toxicity for P-25 and P-125, compared to the higher concentrations used in samples P-0 and P-5.

After 24 hours, G-0 showed no adherence to substrate and no clumping; while G-5, G-25 and G-125 showed increasing levels of adherence of approximately 60%, 80% and 100%, respectively. The PEG treatments and the control were also 100% adhered.

TB staining at 24 hours showed all PLL treatments to have less than 10% viability, while the treatments with PLL-PEG copolymer showed a viability of greater than 70%. Thus the attachment of PEG to PLL substantially alleviates the PLL toxicity; this effect is apparent at very low concentrations (P-125=0.0008% PLL; G-125=0.0024%).

Example IV
Effect of PLL and PLL-PEG on Confluent Monolayers of Fibroblasts

In order to assess, in a more realistic (although in vitro situation), the effects of PLL and PLL-PEG copolymer of the invention on cells which would normally be present in a flattened spread morphology (and not in a rounded morphology), confluent monolayers of HFF were treated with solutions P-0, P-5, G-0, G-5, PEG 20M, and a control (fibroblast culture medium). The cells were exposed to these solutions for 10 minutes, followed by a rinse with HBS, then fibroblast culture medium was returned to the culture dishes.

Short-term observation 15 minutes after treatment showed the P-0 treated cells sloughing off the culture substrate, with approximately 90% of all cells in suspension at 20 minutes.

About 2–5% of cells treated with P-5 were detached from the surface within the same 15 minute period.

HFF treated with solutions G-0, G-5 and PEG 20M showed no appreciable difference from the control cells.

These results indicate that PLL (at 0.1%) is clearly toxic to HFF, while similar concentrations of PLL modified with PEG show no harmful effects to confluent monolayers of cells. It is noteworthy that the P-5 treatment showed only mild toxicity to spread, confluent fibroblasts, indicating that they may be less susceptible to toxic macromolecules in this state rather than in suspension.

Example V
Reversal of PLL-PEG Binding to Cells with Polyanions

It was possible, by addition of heparin sulfate or chondroitin sulfate, to reverse the effect of PLL and PLL-PEG on HFF. Thus, addition of 2.5 U/ml of heparin to the fibroblast culture medium soon after treatment with PLL caused disaggregation of the HFF clumps and resulted in cells that were able to adhere to tissue culture substrates. If, however, the addition of heparin was postponed until several hours after the PLL treatment, reversibility was not possible because the cells had succumbed to PLL toxicity.

This however, was not the case with the PLL-PEG copolymer if the present invention. The nonadhesive, non-aggregating nature conferred upon the fibroblasts by treatment with PLL-PEG copolymer was found to be reversible at least 48 hours after the initial treatment, clearly indicating that these anchorage dependent cells were still alive, despite the fact that they were not adhered to a substrate.

Example VI
Resistance of PLL-PEG Treated Cells to Specific Antibodies as Indicators of Conferred Immune Protection Fibroblasts have receptors for the protein vitronectin on their surfaces. Vitronectin is a cell adhesion molecule (CAM). This receptor (called $\alpha V$-$\beta 3$) can be targeted with an antibody, anti αV-β3, a rabbit polyclonal. A fluorescently conjugated secondary antibody to anti αV-β3 (e.g., rhodamine conjugated anti IgG, goat anti-rabbit) would permit the visualization of these receptors on the cell surface.

Untreated HFF, PLL treated HFF, and PLL-PEG treated HFF were incubated with anti αV-β3 polyclonal antibody, followed by incubation with the secondary antibody, then observed at the appropriate excitation wavelengths under a microscope. It was observed that the untreated and PLL treated cells showed strong fluorescence, while the PLL-PEG treated cells fluoresced at a much lower level. This observation indicates that the approach of the antibody to the cell is hindered by the presence of PEG.

PLL by itself was found not to affect the receptor-ligand interaction.

Based on the above-described experiments, it is likely that the prevention of protein binding to these cells will render them immunologically unrecognizable.

Example VII

Transplantation of PLL-PEG Treated Allogeneic Islets in Rats as a Model for Immunoprotectivity Rat islets were isolated employing techniques known in the art [see, for example, Lacy and Kostianovsky in Diabetes 16:35 (1967)]. The isolated islets were treated with 0.3% PLL-PEG as described above (see Example II), and transplanted by injection into the peritoneal cavity of diabetic rats. Diabetes was induced by treatment with streptozotocin. Controls were injected with untreated rat islets. Blood glucose levels of these rats were monitored at first on an hourly basis, and then on a daily basis for several weeks. It was found that the control rats had a reversal of diabetes (indicated by normal glucose levels) for 3–4 days following which the graft failed due to rejection. On the other hand, the rats injected with the PLL-PEG copolymer treated islets showed a continuous reversal of diabetes for several weeks, indicating that the treatment of these cells with PLL-PEG copolymer was effective in immunoprotecting the islets.

Example VIII

Crosslinkable Graft Copolymers

A variation on the above theme for the surface treatment of cells is one in which the PLL-PEG graft copolymer has on its structure polymerizable groups such as the acrylate group. The presence of this group on the graft copolymer facilitates polymerization or crosslinking following the absorption of the copolymer onto the cell surface through ionic interactions. The resultant covalently crosslinked network is significantly more stable than the ionically attached graft copolymer. Thus the immunoprotective properties conferred upon the cell by absorption of PLL-PEG on its surface are no longer transient as may be expected through an ionic interaction, but are permanent due to the formation of intermolecular and intramolecular covalent crosslinks formed with the PLL-PEG.

Synthesis of these polymerizable copolymers could have two possible strategies. One involves the synthesis of a PEG that is heterobifunctional, i.e., one end is. functionalized with CDI (1,1-carbonyldiimidazole; or other electrophilic derivative) and the other with acryloyl chloride (the reaction of PEG with acryloyl chloride is described below). This technique allows the synthesis of a PLL-PEG graft copolymer in which the free end of PEG contains a polymerizable double bond. The second strategy involves the preparation of PLL-PEG as described above, and the subsequent reaction of the copolymer with acryloyl chloride to add polymerizable groups. In this case the addition of polymerizable groups to the copolymer is nonspecific, i.e., the substitution occurs on the free end of the PEG as well as on the amines on polylysine.

The reaction of PEG with acryloyl chloride proceeds to completion in about 24 hours when carried out at 50° C. For example, mono-CDI functionalized PEG (i.e., CDI-PEG-OH, prepared as described in Example I) was reacted with an equimolar amount of acryloyl chloride in dry dichloromethane solvent. The reaction was carried out in a round-bottom flask under an inert atmosphere at constant reflux for 24 hours. The resulting product was purified by precipitation with diethyl ether, then dried in a vacuum oven.

Alternatively, PLL-PEG could be treated with acryloyl chloride. In this situation, acrylate substitution would occur on both the PEG chains and the PLL backbone (via the amine groups thereof).

Photopolymerization is the method of choice for covalent crosslinking of the graft copolymer following attachment to the cell surface. Following attachment of the graft copolymer to the cell surface the treated cells are transferred to a physiological buffer solution containing ethyl eosin (EE, 0.1 μM to 0.1 mM), triethanolamine (TEA, 0.1 mM to 0.1M), and optionally a comonomer (e.g. 1-vinyl 2-pyrrolidinone (VP) at a concentration in the range of about 0.001 to 1.0%, when used). This solution containing islets is well mixed and exposed to a mercury lamp (100 watt) with a bandpass filter (500–560 nm) for approximately 3 minutes. This causes crosslinking of the copolymer on the surface of the cell resulting in the immunoprotective layer. The cells are then transferred to culture.

An alternative technique involves the incubation of the copolymer treated cells with a solution of EE (0.1 μM to 0.1 mM) in physiological buffer for approximately two minutes. In this step the EE complexes with the positively charged polycation on the cell surface. After rinsing in buffer the cells are transferred to a physiological buffer solution containing TEA (conc. as above), and a comonomer e.g. VP (optional). This solution containing islets is well mixed, polymerized as before, and transferred to culture.

Example IX

PLL-PEG Solutions in Organ Preservation Media

As noted above, PEG 20M has been used in the preservation of organs. The basis of its activity, though not clearly understood, is believed to be the binding of PEG to cell surface molecules through nonspecific hydrophobic interactions. The PLL-PEG copolymer of the present invention, however, interacts directly through ionic interactions with cell-surface moieties bearing a negative charge. Thus, tissues and organs may be flushed with a solution containing the PLL-PEG copolymer prior to transplantation to, in effect, 'coat' the tissues with PEG, thereby providing an immunoprotective and organ-protective effect.

Example X

Stabilization of Liposome with PLL-PEG for Longer Circulation Times and Increased Biocompatibility Lipid vesicles or liposomes have been investigated extensively as systems for drug delivery (Gregoriadis, 1987). The commonly used phospholipids that comprise liposomes, such as phosphatidyl choline, phosphatidyl serine, dilaurylphosphatidic acid, and phosphatidylglycerol are negatively charged at physiological pH. The interaction of polycations such as PLL with the negatively charged phospholipids has been studied quite extensively with regard to conformational changes induced in PLL and consequent stability (Fukushima et al., *Biophysical Chemistry* 34:83 (1989); Houbre et al., *Biophysical Chemistry* 30:245 (1988)

). Stability of liposomes in physiological conditions is a major focus of researchers investigating drug delivery. Although PLL may be used to stabilize lysosomes in vitro, PLL coated liposomes in vivo are likely to be rapidly overgrown or ingested by macrophages due to the adhesive nature of PLL, thus making them ineffective for the controlled release of drugs. In addition, liposomes may also be destroyed by uptake by the reticuloendothelial system. The addition of the graft copolymers of the present invention to the surface of the liposome is likely to prevent this uptake.

The replacement of PLL by the PLL-PEG copolymer of the present invention, however, promises to provide a liposome that is stable not only due to interactions between negatively charged phospholipid and positively charged PLL, but also because the PLL-PEG copolymer will prevent interactions with proteins, and therefore prevent interactions with cells such as macrophages. This should result in liposomes with long circulation times which can therefore deliver drugs in a controlled fashion.

Example XI
Patterned Surfaces for Neural Networks

Investigators in neurology have tried to generate in vitro networks of neurons on culture dishes. A problem has been to generate patterned surfaces that are preferentially adherent to cells in order to design 'biological circuits.' By creating a mask of the pattern desired, and applying it to the culture substrate, followed by treatment of the surface with PLL-PEG copolymer, one can selectively leave the desired pattern adhesive to cells, while the rest of the available surface is rendered nonadhesive to cells.

While the invention has been described in detail with reference to certain preferred embodiments thereof, it will be understood that modifications and variations are within the spirit and scope of that which is described and claimed.

That which is claimed is:

1. A graft copolymer comprising:
   a polycationic species;
   at least one water-soluble polymer grafted onto said polycationic species; and
   at least one functional group capable of undergoing free radical polymerization.

2. A graft copolymer according to claim wherein said water-soluble polymer is selected from polyalkylene glycol (PAG), polyvinyl alcohol (PVA), poly(hydroxyethyl methacrylate) (pHEMA), polyacrylic acid (PAA), poly(acrylamide), poly(vinyl pyrrolidone) (PVP), poly(ethyl oxazoline) (PEOX), polysaccharides, or copolymers of any two or more thereof.

3. A graft copolymer according to claim 2 wherein said water-soluble polymer is PAG.

4. A graft copolymer according to claim 1 wherein said polycationic species is selected from the group consisting of:
   polyethyleneimine, polyallylamine, polyetheramine, polyvinylpyridine;
   polysaccharides having a positively charged functionality thereon;
   polyamino acids selected from the group consisting of poly-L-histidine, poly-im-benzyl-L-histidine, poly-D-lysine, poly-DL-lysine, poly-L-lysine, poly-$\epsilon$-CBZ-D-lysine, poly-$\epsilon$-CBZ-DL-lysine, poly-$\epsilon$-CBZ-L-lysine, poly-DL-ornithine, poly-L-ornithine, poly-$\delta$-CBZ-DL-ornithine, poly-L-arginine, poly-DL-alanine-poly-L-lysine, poly(-L-histidine, L-glutamic acid)-poly-DL-alanine-poly-L-lysine, poly(L-phenylalanine, L-glutamic acid)-poly-DL-alanine-poly-L-lysine, and poly(L-tyrosine, L-glutamic acid)-poly-DL-alanine-poly-L-lysine;
   random copolymers of L-arginine with tryptophan, tyrosine, or serine;
   random copolymers of D-glutamic acid with D-lysine,
   random copolymers of L-glutamic acid with lysine, ornithine, or mixtures of lysine and ornithine; and
   mixtures of any two or more thereof.

5. A graft copolymer according to claim 1 wherein said polycationic species is selected from the group consisting of polylysine and polyornithine.

6. A graft copolymer according to claim 1 wherein said polycationic species has a molecular weight in the range of about 200 up to about 1,000,000.

7. A graft copolymer according to claim 6 wherein said polycationic species has a molecular weight in the range of about 1,000 up to about 100,000.

8. A graft copolymer according to claim 7 wherein said polycationic species has a molecular weight in the range of about 5,000 up to about 50,000.

9. A graft copolymer according to claim 1 wherein said water-soluble polymer has a molecular weight in the range of about 200 up to about 1,000,000.

10. A graft copolymer according to claim 9 wherein said water-soluble polymer has a molecular weight in the range of about 500 up to about 100,000.

11. A graft copolymer according to claim 10 wherein said water-soluble polymer has a molecular weight in the range of about 1,000 up to about 50,000.

12. A graft copolymer according to claim 1 wherein said functional group is covalently attached to said polycationic species.

13. A graft copolymer according to claim 1 wherein said functional group is covalently attached to said water-soluble polymer.

14. A graft copolymer according to claim 1 wherein said functional group is a vinyl group, an acrylate group, or a methacrylate group.

15. A graft copolymer according to claim 1 wherein there are about 10 to about 20 water-soluble polymers attached to said polycationic species.

* * * * *